(12) United States Patent
Moxon et al.

(10) Patent No.: US 6,834,200 B2
(45) Date of Patent: Dec. 21, 2004

(54) CERAMIC BASED MULTI-SITE ELECTRODE ARRAYS AND METHODS FOR THEIR PRODUCTION

(75) Inventors: Karen Anne Moxon, Philadelphia, PA (US); John K. Chapin, Riverton, NJ (US)

(73) Assignee: Philadelphia, Health & Education Corporation, Philadelphia, PA (US)

( * ) Notice: Subject to any disclaimer, the term of this patent is extended or adjusted under 35 U.S.C. 154(b) by 276 days.

(21) Appl. No.: 09/999,601

(22) Filed: Oct. 19, 2001

(65) Prior Publication Data

US 2002/0106496 A1 Aug. 8, 2002

Related U.S. Application Data

(60) Provisional application No. 60/241,630, filed on Oct. 19, 2000.

(51) Int. Cl.[7] .............................. A61B 5/042; A61N 1/05
(52) U.S. Cl. ........................ 600/373; 600/377; 600/378; 607/116; 607/117
(58) Field of Search ................................. 600/373, 377, 600/378; 607/116, 117

(56) References Cited

U.S. PATENT DOCUMENTS

| | | | | | |
|---|---|---|---|---|---|
| 4,133,735 A | * | 1/1979 | Afromowitz et al. | ........ | 600/395 |
| 4,461,304 A | * | 7/1984 | Kuperstein | .................. | 600/378 |
| 4,969,468 A | * | 11/1990 | Byers et al. | ................ | 600/373 |

OTHER PUBLICATIONS

BeMent et al., "Solid–State Electrodes for Multichannel Multiplexed Intracortical Neuronal Recording", IEEE Trans. Biomed. Eng. 1986 33(2):230–240.

Campbell et al., "A Silicon–Based, Three–Dimensional Neural Interface: Manufacturing Processes for an Intracortical Electrode Array", IEEE Trans. Biomed. Eng. 1991 38(8):758–768.

Moxon et al. Designing a Brain–Machine Interface for Neuroprosthetic Control in *Neural Prosthesis for Restoration of Sensory and Motor Function* Eds K.A. Moxon and J.K. Chapin, CRC Press, Boca Raton, FL, 2000.

Najafi et al., "A High–Yield IC–Compatible Multichannel Recording Array", IEEE Trans. Electron Dev. 1985 32(7):1206–1211.

Najafi et al., "Scaling Limitations of Silicon Multichannel Recording Probes", IEEE Trans. Biomed. Eng. 1990 37(1):1–11.

Pickard R.S. and Welberry T.R., "Printed Circuit Microelectrodes and Their Application to Honeybee Brain", J. Exp. Biol. 1976 64:39.

Pickard R.S., "A Review of Printed Circuit Microelectrodes and Their Production", J. Neurosci. Meth. 1979 1:301–319.

*Methods for simultaneous neuronal ensemble recordings* Eds. M.A.L. Nicolelis, CRC Press, Boca Raton, FL 1999.

* cited by examiner

*Primary Examiner*—Lee S. Cohen
(74) *Attorney, Agent, or Firm*—Licata & Tyrrell P.C.

(57) ABSTRACT

Ceramic based multi-site electrode arrays of a polished ceramic substrate patterned with recording sites and bonding pads which are connected via conducting lines are provided. Methods for producing these electrode arrays and using the electrode arrays to record or stimulate multiple neurons in a mammal are also provided.

5 Claims, 2 Drawing Sheets

CERAMIC BASED MULTI-SITE ELECTRODE ARRAYS AND METHODS FOR THEIR PRODUCTION

INTRODUCTION

This application claims the benefit of priority from U.S. Provisional Application Ser. No. 60/241,630, filed Oct. 19, 2000.

This invention was supported in part by funds from the U.S. government (DARPA-ONR Grant No. N00014-98-1-0679) and the U.S. government may therefore have certain rights in the invention.

FIELD OF THE INVENTION

The present invention relates to ceramic based multi-site electrode arrays comprising a polished ceramic substrate which is patterned with metal recording sites, conducting lines and bonding pads. The electrode arrays of the present invention are useful in recording large numbers of neurons simultaneously in mammalian central nervous system tissue. Further the electrode arrays of the present invention are useful for chronic stimulation of small regions of neural tissue using small currents. Methods for producing the multi-site ceramic based electrode arrays via reverse photolithography are also provided.

BACKGROUND OF THE INVENTION

Although many different types of electrodes have been designed for recording and stimulating mammalian central nervous system tissue (see e.g. Moxon, K.A. Multiple-site recording electrodes in *Methods for simultaneous neuronal ensemble recordings* Eds. M.A.L. Nicolelis, CRC Press, Boca Raton, Fla. 1999), traditional chronic recording electrodes consist of a gold, platinum or stainless steel wire coated with an insulating material, usually Teflon, except at the tip. While these electrodes function adequately in many situations, they suffer drawbacks that reduce their usefulness as neural interface devices. These drawbacks include a low recording site (RS) to neuronal tissue displaced (NTD) ratio, difficulty of integrating on board electronics sufficiently close to the electrode to reduce noise, and the inability to produce quality microwire electrodes for neural recording using batch processing. Generally these electrodes are made by hand, resulting in considerable variation in the recording characteristics of each electrode tip. Further, since on board electronics will ideally be included, a wide range of electrical characteristics of the electrode results in difficulties properly matching impedances.

Thin-film electrodes have also been developed to record neuron activity (Pickard, R. S. and Welberry, T. R. J. Exp. Biol. 1976 64:39; Pickard, R. S. J. Neurosci. Meth. 1979 1:301; Llinas et al. Implantable monolithic wafer recording electrodes for neurophysiology in *Brain unit activity during behavior*, Eds. M. I. Philips and C. C. Thomas, I11, 1973; Najafi et al. IEEE Trans. Electron Dev. 1985 32:1206; Wise, K. D. and Angell, J. B. IEEE Trans. Biomed. Eng. 1970 BME-17(3):238; Campbell et al. Proc. 27th Annu. Rocky Mountain Bioeng. Symp. and the 27th Int. ISA Biomed. Sci. Inst. Symp. Denver, Colo., Apr. 6–7, 1990, 161; BeMent et al. IEEE Trans. Biomed. Eng. 1986 33(2):230; and Campbell et al. IEEE Trans. Biomed. Eng. 1991 38(8):758) However, the majority of these electrodes are built on silicon substrates and have not been shown to be useful for chronic stimulation and recording of single neurons.

In the present invention, a multi-site electrode array is provided which comprises a polished ceramic substrate patterned with recording sites, conducting lines and bonding pads. This thin film electrode has the ability to maintain the brain-electrode interface at a high RS/NTD ratio, records chronically from single neurons for up to 3 months, and uses a substrate material and insulation that is strong and resistant to the brain microenvironment. The electrode of the present invention is the same size as a single microwire but has multiple recording sites and can be integrated with onboard electronics in a very large scale integration (VLSI) circuit.

SUMMARY OF THE INVENTION

An object of the present invention is to provide a ceramic based multi-site electrode array useful in recording and/or stimulating large numbers of neurons simultaneously.

Another object of the present invention is to provide a method for producing ceramic based multi-site recording electrode arrays comprising patterning a polished ceramic substrate with recording sites, conducting lines and bonding pads via image reverse photolithography following by application of a metal layer and an insulating layer.

BRIEF DESCRIPTION OF THE FIGURES

FIG. 1A shows one embodiment of the ceramic based multi-site electrode array comprising four recording sites spaced 0.2 mm apart at the tip of the array. As depicted in FIG. 1A, each recording site is connected to a bonding pad at the opposite end of the array via a conducting line.

FIG. 1B shows an enlarged view of the recording site area of the electrode array depicted in FIG. 1A.

DETAILED DESCRIPTION OF THE INVENTION

Figure 1A:
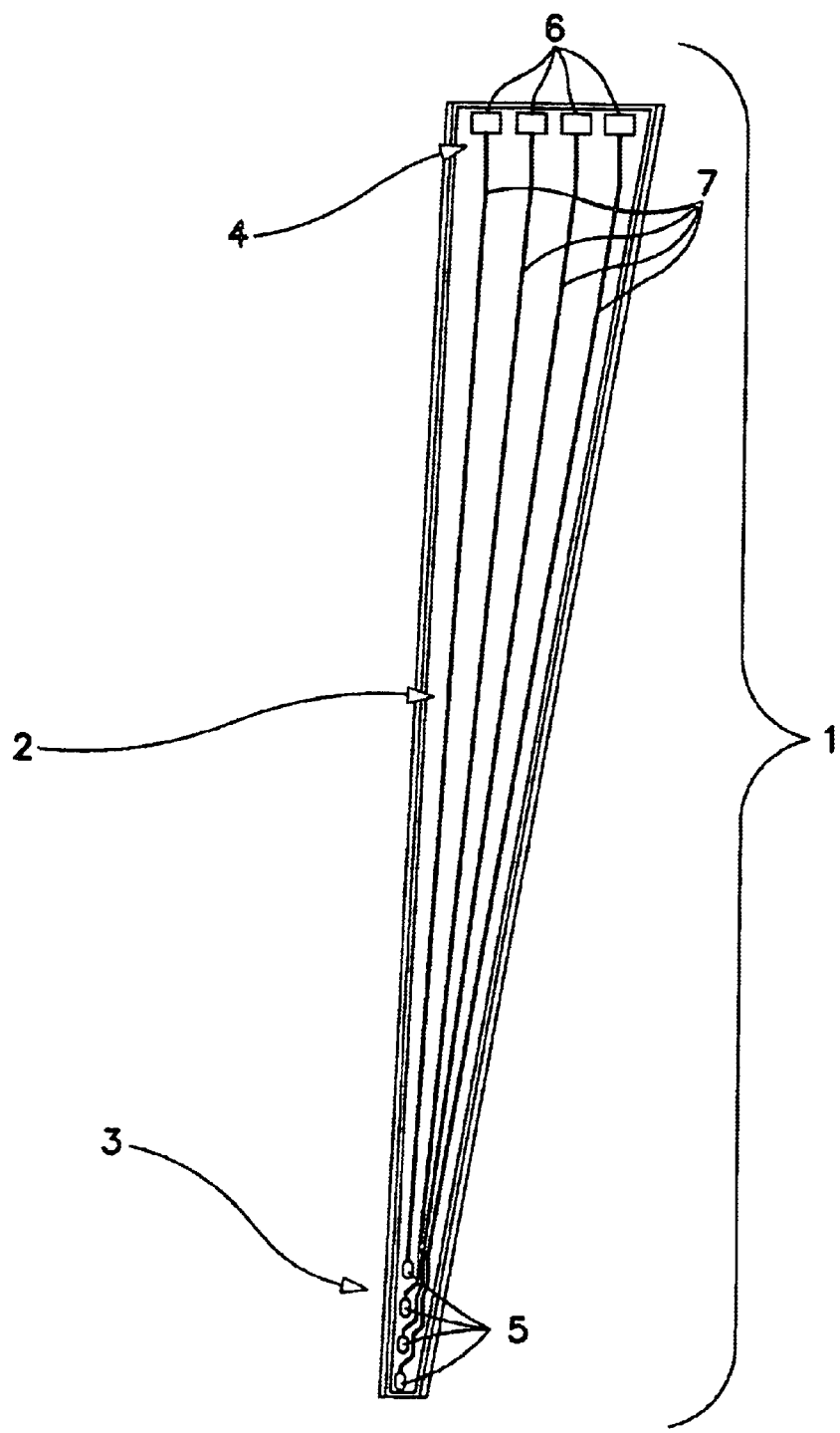
FIGS. 1A and 1B are schematic drawings of ceramic based multi-site electrode (CBMSE) arrays of the present invention.

Ceramic based multi-site electrode (CBMSE) arrays and methods of producing these arrays have now been developed for use in recording and/or stimulating large numbers of neurons simultaneously in chronic freely moving mammals.

The CBMSE arrays of the present invention comprise a polished ceramic substrate, preferably less than or equal to 50 microns in thickness with a range of 35 to 50 microns being preferred, having a narrow tip at one end ranging up to 0.1 mm in width and preferably pointed to cut through neural tissues, and a wider region at the opposite end approximately twice the width of the narrow tip. The wider region contains the bonding pads, does not enter the neural tissue and is sized to be large enough to provide contacts for on-board electronics such as VLSI. It is preferred that the ceramic substrate be of a purity which is inert in the brain microenvironment so that local brain signal are not conducted. Accordingly, in a preferred embodiment of the present invention, the ceramic substrate comprises 99.6% pure alumina.

The polished ceramic substrate is patterned with multiple recording sites, preferably 2 to 32 recording sites, at the narrow tip of the substrate. Each recording site is connected to a bonding pad placed at the opposite wider end of the substrate via a conducting line which runs from the recording site to the bonding pad. A metal layer, preferably platinum, is applied to the entire pattern to produce the recording sites, conducting lines and bonding pads which form the electrode. A first insulating layer, preferably alumina, is then applied to the metal conducting lines and bonding pads. In a preferred embodiment, the alumina is ionized using a process of ion-beam assisted deposition. Application of a second insulating layer comprising polyimide to the conducting lines is also preferred. To complete the array, the bonding pads are attached to second stage recording equipment which amplifies and filters the signal. Examples of second stage recording equipment include, but are not limited to, the MNAP system (Plexon, Inc.), Experimenters Workbench (DataWave Technologies), and Alpha-Map (Alpha omega). The CBMSE arrays of present invention are preferably sized to mimic single microwires. However, unlike single microwires, the multiple recording sites of the CBMSE arrays can be integrated with onboard electronics in a VLSI circuit (Moxon et al. Designing a Brain-Machine Interface for Neuroprosthetic Control in *Neural Prosthesis for Restoration of Sensory and Motor Function* Eds K. A. Moxon and J. K. Chapin, CRC Press, Boca Raton, Fla., 2000) to permit large numbers of neurons to be measured simultaneously.

Unlike silicon which has been typically used as the substrate in thin-film electrodes, ceramic does not act as a conductor, is stronger than silicon, and more rigid thereby aiding in inserting the electrode through the dura into deep brain structures. In addition, the insulating layer of alumina can be ionized using a process of ion-beam assisted deposition to provide an insulating layer over the conducting lines which is superior to traditional silicon nitride. More specifically, the dielectric properties of alumina are lower than silicon nitride, thus reducing the capacitive coupling between conducting lines and allowing the space between features to be reduced. Further, ion-beam assisted deposition of alumina effectively seals the metal conducting lines in a capsule of inert ceramic. Such insulation allows the electrode arrays of the present invention to exist in the saline microenvironment of the brain for decades.

An embodiment of the CBMSE array of the present invention is depicted in FIG. 1A. As shown in this Figure, the CBMSE array 1 is comprised of a ceramic substrate 2 having a narrow tip 3 at one end of the substrate 2 and a wider region 4 at the opposite end of the substrate 2. In this embodiment, four recording sites 5, are vertically arranged at the narrow tip 3 of the substrate 2. However, as will be understood by those of skill in the art upon reading this disclosure, various quantities and configurations of recording sites can be accommodated by this invention, according to the desired testing methods. In the embodiment depicted in FIG. 1A, four bonding pads 6 are horizontally arranged at the wider region 4 at the opposite end of the substrate 2. The bonding pads 6 and the recording sites 5 are connected via conducting lines 7.

Figure 1B:
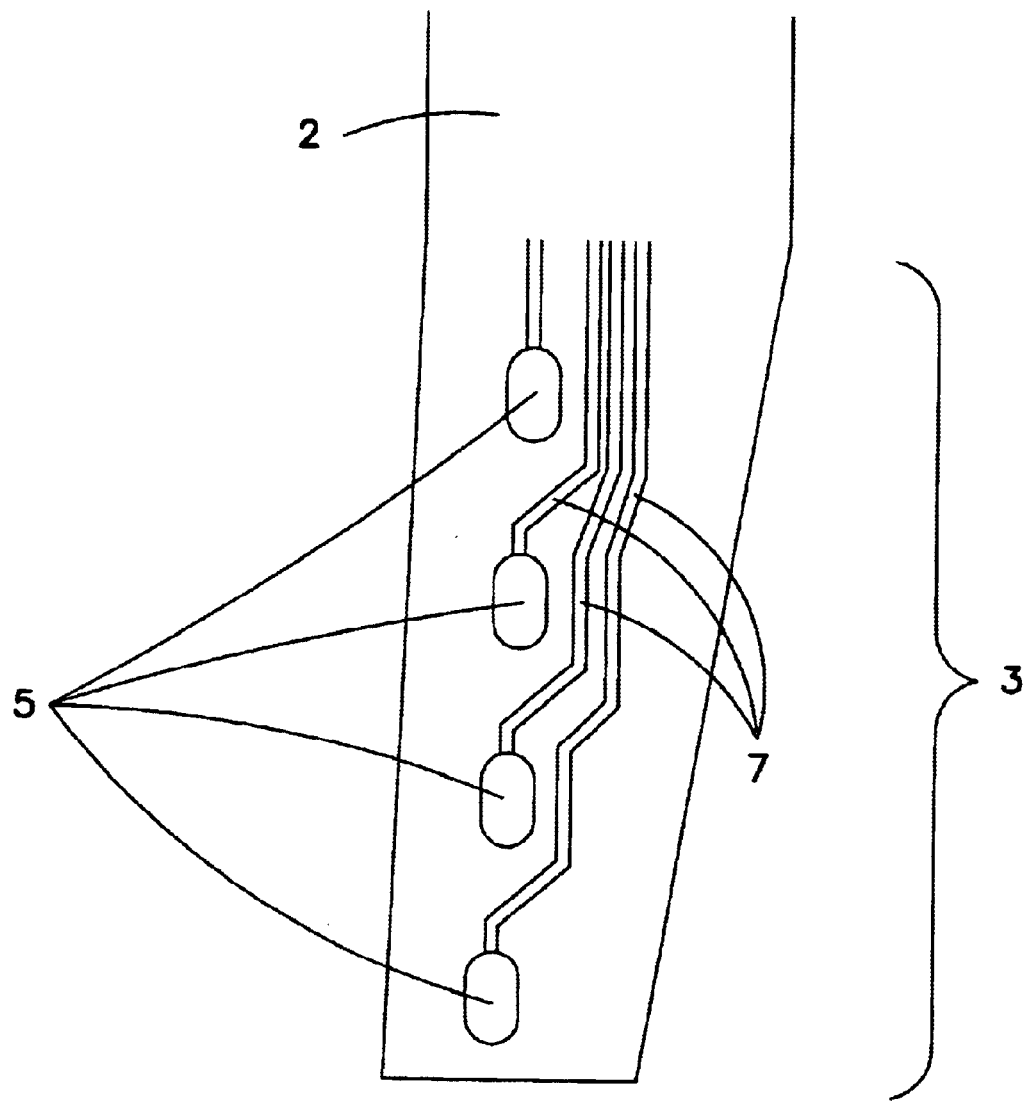

FIG. 1B shows an enlarged diagram of the narrow tip 3 of the substrate 2 of FIG. 1A. In this embodiment which comprises four recording sites, each recording site 5 is 0.022 mm×0.080 mm in size. However, as will be understood by those of skill in the art upon reading this disclosure, recording site size can be adjusted depending upon the number of sites, the size of the substrate and the use for the electrode array. The electrodes are preferably arranged to maximize the number of neurons recorded. Accordingly, it is preferred that the recording sites be arranged on the substrate to match the neural tissue. For example, in high density neuronal layers, recording sites are preferably clustered together to provide optimal recording. In the embodiment depicted in FIG. 1, the recording sites are positioned linearly in vertical fashion 0.2 mm apart. In this embodiment, the width of the ceramic substrate 2 at the tip 3 is 0.0664 mm; the width of the ceramic substrate 2 at the final recording site is 0.113 mm; and the width of the ceramic substrate 2 at the wider region 4 at the top of the substrate where the bonding pads are located is 750 microns. In general, however, the conducting lines are at least 5 microns wide and are spaced 5 microns apart (Najafi et al. IEEE Trans. Biomed. Eng. 1990 37(1):1). Accordingly, the width of the ceramic substrate can be adjusted depending upon the number of recording sites.

The present invention also provides methods for producing these CBMSE arrays. In these methods, the polished ceramic substrate is patterned with the recording sites, conducting lines and bonding pads. In a preferred embodiment, this patterning is performed directly onto the ceramic substrate via image reverse photolithography. In standard photolithography, the mask defines the metal pattern to be adhered to the substrate allowing exposure of the photoresist where metal will adhere to the substrate. Thus, traditional photolithography produces a positive sidewall angle, narrower at the bottom (closest to the substrate) and wider at the top, and the size of the resist features is limited. In reverse photolithography, the mask is the reverse of traditional photolithography, initially exposing the photoresist where the metal will not adhere to the substrate. Accordingly, image reverse photolithography produces a negative sidewall angle that is crucial for small resist features of less than 10 microns such as the conducting lines and cannot be achieved with standard photolithography procedures. Since the negative sidewall angle is wider at the bottom closest to the substrate, resist features as small as 2 microns can be made. Thus, reverse image photolithography allows for precise control of the resist wall angles and improves the resolution of the final features applied to the substrate. Further, since the initial mask is the reversal of the standard positive mask, the photoresist exposed is the area where the metal is to adhere to the substrate.

In this method, the ceramic substrate with the photoresist is exposed to ultraviolet (UV) light, followed by flooding with an amine vapor that binds to the exposed resist, neutralizing it by forming a carboxylic acid that is highly insensitive to development. The first two steps, UV exposure using the reverse mask followed by flood amine vapor neutralizes the exposed photoresist essentially creating an in situ mask in the resist film. Time of exposure to the UV light is dependent upon the feature size and can be adjusted routinely by one of skill in the art. Using the reverse mask which is patterned where metal is not desired, the ceramic substrate is exposed to UV light, converting the exposed photoresist (areas where metal will not be patterned) to carboxylic acid. The mask is removed and the substrate is flood exposed with an amine vapor that binds to the exposed resist, neutralizing it by forming a tightly held matrix of amide that is highly insensitive to further UV development. The substrate then contains a pattern of unreactive photoactive compound from binding with the amide that is adjacent to unexposed areas of photoresist, that does not react with the amine vapor, and is available for exposure. This unreactive area defines the recording site, conducting lines and bonding pads. The entire substrate is then exposed to UV light again. The photoresist exposed in this last step is removed during development exposing the substrate to the pattern of recording sites, conducting angles and bonding pads with a negative sidewall angle. An added benefit of this process is that the width of the features to be patterned are now well defined down to the level of the substrate.

Once the ceramic substrate is patterned with appropriate resist features that define the recording sites, conducting lines and bonding pads, the metal is applied to the substrate, completely covering the exposed regions and the resist features. The metal applied is preferably platinum because it has been shown to cause the least histological damage for long-term implants. However, other metals such as gold and carbon can also be used. The metal is deposited onto the ceramic substrate where the resist has been developed away and resides directly on the substrate surface. The negative sidewall angle results in a thinner layer of metal at the step from substrate surface to resist. The unwanted metal, along with the underlying photoresist is then removed using a lift-off procedure. In this procedure, the substrate is submersed in a commercially available photoresist stripper so that the photoresist expands thereby cracking the surface of the metal at the step and allowing the stripper access to the photoresist. The remaining photoresist is lifted off along with any unwanted overlying metal. The metal left behind defines the recording sites, conducting lines and the bonding pads of the electrode.

An important element of an electrode interface subassembly is the insulation used to protect the metal conducting lines from the brain microenvironment. Any breach in the insulation along the length of an electrode can destroy the integrity of the recording site by shorting it out. The only exposed sites on the electrode should be the recording sites. Further, the recording sites must remain insulated from each other. However, the exposed metal surface of the recording site is a conducting medium and if there is any breach in the insulation exposing a conducting line, there will be cross-talk noise in the signal from this damaged site. The effects of the brain micro-environment on the integrity of the insulation is also an important consideration. The electrode is essentially soaking in a salt solution. Very few insulating materials are impermeable to the extracellular fluid, and this is an important problem for long-term recording devices. However, alumina ($Al_2O_3$) has been indicated to be a superior insulating material.

Accordingly, following application of the metal layer, it is preferred that an insulating layer of alumina be applied to the conducting lines of the ceramic substrate. In a preferred embodiment, the insulating layer of alumina is applied using ion-beam assisted deposition. In this procedure, the alumina is ionized using an electron beam. The insulation procedure is similar to the metalization procedure. A second photomask is used that leaves only the recording sites and the bonding terminals exposed. Photoresists are applied over the recording site, conducting lines and bonding pads and developed using this photomask so that the conducting lines and bonding pads are protected. The entire substrate is then layered with an insulator using ion beam-assisted deposition, and finally the resist over the recording sites and bonding pads is removed, simultaneously removing the insulator. The individual electrodes are then released from the substrate by laser cutting. This effectively encases the conducting lines in ceramic.

To complete the assembly, the bonding terminals are attached to second stage recording equipment. The integrity of these bonds affects the recording capability of the entire electrode. Most simply the electrodes can be connected to a rigid connector using ultra-sonic wire bonding. However, a more flexible connection such as a flexible cable may be preferred to allow the electrode to float more freely in the neural tissue and move with the brain inside the skull cavity. After final assembly, it is preferred that a coating of polyimide be applied onto the electrode as an added layer of insulation protection.

CBMSE arrays as depicted in FIG. 1A were prepared in accordance with this method and characterized.

Scanning electron micrographs of the surface of the ceramic substrate after the final insulation process but before separating from substrate showed that the recording sites were well defined and the insulation was not breached. After separating from the substrate and mounting on a connector, each electrode was visually inspected under a microscope at 20x. There were no obvious nicks or cracks in the electrodes due to the cutting process.

These electrode arrays were also tested in vivo. In these experiments, one or more blunt tip ceramic based multi-site electrode arrays such as depicted in FIG. 1A were implanted slowly into the cortex of a test animal without causing major tissue depression. The arrays remained rigid as they passed through the pia layer. Neural recordings could be detected on each recording site in sequence as the electrodes were lowered into the brain. Neural responses to whisker stimulus were qualitatively evaluated and, as expected, depended on the level of anesthesia. After the electrodes were cemented in place, the ability of each recording site to still detect the neural responses to whisker stimulation was confirmed.

The surgery for single array implantation was relatively short and recordings in the animals were conducted from 24 hours post-surgery. The animals were lightly anesthetized using NEBUTAL and a headstage (Plexon Inc.) was inserted into the array connector. The animals' heads were placed in a support stand and single neurons were discriminated from each recording site. For these single array implants more than one neuron could be discriminated from more than half of the recording sites.

For surgery when two arrays were implanted, the animals were allowed three days to recover from the initial dose of anesthesia. For subsequent recording sessions, animals were anesthetized, headstages were inserted into the array connector and the animals were placed in a head support stand. Animals were recorded everyday for three days, then once per week for four weeks, at six weeks, 2 month and finally at 3 months. Individual neurons could be recorded from each recording site for up to six weeks. At the six week point, 20 percent of recording sites were not as effective at discriminating individual neurons. However, neural clusters could be discriminated and when computer controlled stimuli were applied, statistically significant peri-event histograms could be generated, suggesting that the electrodes could still detect biologically relevant neural signals. At 2 months half of the recording sites were still capable of discriminating single neurons and at three months almost 20 percent of the recording sites still had discriminable neurons. At 6 months impedances were checked for a final time. Overall impedances increased, final impedances were 11.74+/−22.0. However, the animals actually fell into 3 groups. One electrode (all four sites) increased dramatically (46.3+/−24.3); two electrodes decreased significantly (0.166+/−0.083); and two electrodes changed little (2.62+/−1.1). The rats were allowed to survive to six months at which point there were no discriminable neurons but the input impedances still were not significantly different from pre-implant conditions. At six months the animals were anesthetized and the brain's perfused with formalin and preserved for subsequent analysis. The electrodes were inspected after being removed from the brain and the electrode with significantly higher impedances and one of the electrodes with significantly lower impedances were incased in scar tissue. These results indicate that these CBMSE arrays can be used for chronic multiple single unit recording in mammals for at least three months.

The following nonlimiting examples are provided to further illustrate the present invention.

EXAMPLES

Example 1
Electrode Design

Ceramic substrates were purchased from Valley Design, and polished to a thickness of 0.0015–0.002 inches.

Example 2
In-vitro Testing of Impedance Measure

The impedance of each recording site was measured, n=280 sites, 4.19+/−3.2 MOhms. When the sites were measured as groups (site 1 vs. site 2 etc) There was no difference between sites. Site 1 4.80+/−3.5; site 2: 4.39+/−3.3; site 3: 4.02; 3.5; site 4: 3.54+/−2.2. t-Tests: site 1 vs site 2: p=0.48; site 2 vs. site 3: p=0.52; site 3 vs. site 4: p=0.33. All impedance measures were made using an Impedance Check instrument from FHC, Inc. (Bowdoinham, Me.).

Example 3
Soak Tests

Four CBMSE arrays whose recording sites (total of 16) had similar input impedances 2.3+/− were sealed in 0.9% saline to test the integrity of the insulation and recording sites over time. There was no significant difference between the initial input impedances and the final input impedances (4.17+/−3.8); t-Test p=0.54.

Example 4
Surgical Implantation of CBMSE Arrays

Each array was implanted in the animal through small craniotomies. Two animals had one array implanted and four animals had two arrays implanted bilaterally into the somatosensory cortex of the rat (whisker barrel field: −2.5 AP, 5.5 ML, coordinate from Bregma). A series of smaller holes were then drilled in the skull for placement of 5 metal screws which provide support for the arrays and a common reference for electrophysiological recordings. Once the craniotomies were completed, a small slit was made in the dura mater just prior to slowly (approximately 100 µm/minute) lowering the electrode array through the pial surface into the cortex. Single and multiunit recordings were performed throughout the implantation procedure to ensure the correct placement of the arrays. The receptive fields of both single neurons and multiunits were qualitatively characterized to define the relative position of each individual array. The arrays were placed so that the recording sites were in layers four and five of the barrel field. Once the most dorsal site on the array reached the lower layers of the cortex, the craniotomy was filled with small pieces of gelfoam and then covered with either bone wax or 4% agar. Once the craniotomy was sealed, the entire array was fixed in position using dental cement. This procedure was repeated several times if a second array was implanted in a neighboring region of the barrel cortex.

What is claimed is:

1. A ceramic based multi-site electrode array for recording and stimulating mammalian central nervous system tissue in vivo comprising a polished ceramic substrate patterned with recording sites and bonding pads which are connected via conducting lines and an insulating layer encasing the conducting lines in inert ceramic but leaving exposed the recording sites.

2. The ceramic based multi-site electrode array of claim 1 wherein the insulating layer comprises $Al_2O_3$.

3. The ceramic based multi-site electrode array of claim 2 wherein the $Al_2O_3$ is ionized using a process of ion-beam assisted deposition prior to layering over the conducting lines.

4. A method for recording or stimulating multiple neurons simultaneously in mammal comprising implanting the ceramic based multi-site electrode array of claim 1 into a mammal.

5. The ceramic based multi-site electrode array of claim 1 produced by a method comprising:
   (a) patterning by reverse photolithography the ceramic substrate with resist features that define recording sites, bonding pads and conducting lines connecting the recording sites and bonding pads;
   (b) applying a metal conductor to the ceramic substrate patterned with the resist features defining the recording sites, bonding pads and conducting lines connecting the recording sites anda bonding pads; and
   (c) submersing the ceramic substrate of step (b) in a photoresist stripper which lifts off unwanted overlying metal and leaves behind metal on the ceramic substrate defining the recording sites, conducting lines and bonding pads; and
   (d) applying an insulating layer to the metal defining the conducting lines of the ceramic substrate.

* * * * *